United States Patent [19]

Esser

[11] Patent Number: 5,368,651
[45] Date of Patent: Nov. 29, 1994

[54] METHOD OF STEAM-TREATING SANITARY SYSTEMS AND/OR FOR DISINFECTING THE PIPELINES OF SANITARY SYSTEMS AND WHIRLPOOL SYSTEM FOR IMPLEMENTING THE METHOD

[75] Inventor: Hans-Peter Esser, Bergheim, Germany

[73] Assignee: Hoesch Metall+Kunststoffwerke GmbH & Co.

[21] Appl. No.: 941,149
[22] PCT Filed: Mar. 12, 1992
[86] PCT No.: PCT/EP92/00549
 § 371 Date: Jan. 14, 1993
 § 102(e) Date: Jan. 14, 1993
[87] PCT Pub. No.: WO92/16243
 PCT Pub. Date: Oct. 1, 1992

[30] Foreign Application Priority Data

Mar. 15, 1991 [DE] Germany ............... 4108539

[51] Int. Cl.⁵ .................. B08B 3/02; B08B 9/00; B08B 9/093
[52] U.S. Cl. .................. 134/22.1; 134/22.11; 134/22.15; 134/169 R; 134/166 R; 134/104.1
[58] Field of Search ............ 134/22.1, 22.11, 22.15, 134/169 R, 166 R, 104.1

[56] References Cited

U.S. PATENT DOCUMENTS

| 3,297,481 | 1/1967 | Newman | 134/22.15 |
| 4,922,937 | 5/1990 | Bloch | 134/22.15 |
| 4,944,919 | 7/1990 | Powell | 422/26 |
| 4,954,179 | 9/1990 | Fränninge | 134/22.1 |

FOREIGN PATENT DOCUMENTS

| 0297246 | 1/1989 | European Pat. Off. |
| 2603976 | 3/1988 | France |
| 3420714 | 12/1985 | Germany |
| 3722281 | 1/1988 | Germany |
| 3902117 | 9/1990 | Germany |
| 3928464 | 3/1991 | Germany |

OTHER PUBLICATIONS

"Production Method of Steam or Hot Water for Cleaner Using Electric Heating Element to Boil Water and Injects Liquid Into Steam to be Heated and Carried by Steam", Derwent Abstract N88-092336.

Primary Examiner—Richard O. Dean
Assistant Examiner—Zeinab El-Arini
Attorney, Agent, or Firm—Spencer, Frank & Schneider

[57] ABSTRACT

A whirlpool system includes a basin defined by basin walls; a pipe system including a central conduit and nozzles coupled to the central conduit and situated in the basin walls and having nozzle outlets directed to the basin; a pressure generator coupled to the central conduit for supplying the nozzles with water and/or air; a mist generator for generating a fluid mist under influence of temperature at normal atmospheric pressure; and an intake conduit coupling the mist generator to the central conduit in a zone of the pressure generator for disinfecting the pipe system and the basin.

19 Claims, 1 Drawing Sheet

METHOD OF STEAM-TREATING SANITARY SYSTEMS AND/OR FOR DISINFECTING THE PIPELINES OF SANITARY SYSTEMS AND WHIRLPOOL SYSTEM FOR IMPLEMENTING THE METHOD

BACKGROUND OF THE INVENTION

The invention relates to a method of steam-treating sanitary systems and/or for disinfecting the pipelines of sanitary systems, particularly the pipelines in whirlpool systems.

The disinfection of the pipelines of whirlpool tubs has in the past been effected, depending on the structural type, either during filling of the tub, in which case, during the filling process, part of the fresh water was reversed to flow out of the tub through the pipe system directly into the drain pipe. By placing shut-off valves at the whirlpool nozzles, it additionally became possible to rinse the pipeline system for a short time under pressure with the aid of the circulating pump, with the water then not being discharged from the pressure side into the tub but into the drain pipe (DE-OS [German Unexamined Published Patent Application] 3,420,714).

In other methods, fresh water mixed with a disinfectant is conducted through the pipe system practically without pressure at the end of the bath immediately after the bath water has been emptied. In this case, however, there exists the drawback, on the one hand, that relatively large quantities of fresh water are required and, on the other hand, the water mixed with the disinfectant also enters the interior of the tub. In this method, a second step is required in which the entire pipe system including the interior of the tub must be carefully rinsed with pure fresh water in order to avoid skin irritation during the next bath (DE-OS 3,722,281).

Finally, it has been attempted to design tightly closable nozzles with which the flow direction can be reversed to flush the pipe system with the aid of the circulating pump under the full pumping pressure so that the mechanical effect of the flowing water is utilized here to prevent the formation of deposits in the pipe system. The problem in this connection is, in particular, that it is not possible for the flowing water to have an influence in the region of the closing mechanisms for the nozzles (German Patent 3,902,117).

It is known from FR 2,603,976.A1 to generate hot steam for household use in a pressure container and to blow the steam out at its intended location. By spraying in a liquid, the temperature is then reduced and the quantity of hot steam to be generated is reduced.

SUMMARY OF THE INVENTION

It is now the object of the invention to create a method for disinfecting pipe systems, particularly the pipes of whirlpool systems, with which the above-described drawbacks are avoided.

This is accomplished according to the invention in that a heated, mist-like fluid medium is produced and introduced into the chamber to be steam-treated or is conducted through the pipe system.

The term "mist-like medium" in the sense of the present invention includes a vapor generated with the aid of a liquid under the influence of temperature, particularly a wet steam or a saturated steam, also a wet steam or saturated steam that is introduced into a carrier stream as well as a fog or an aerosol, that is, a liquid in ultra-fine dispersion that is introduced into a heated carrier gas.

Surprisingly it was found that, for example, a pipeline contaminated with *Pseudomonas aeruginosa* was free of bacteria after being charged with steam as the mist-like medium at a temperature between 70° and 90° C. for a period of only a few minutes.

The particular advantage of this method is that, instead of large quantities of flushing water and the use of chemicals, only a small quantity of liquid and small amounts of energy are required to produce the mist-like medium. In a simple manner, the mist-like medium may here be conducted through the entire pipe system and thus flow freely through the swirl nozzles into the interior of the tub as well as through the pressure conduit, the circulating pump and the suction opening into the interior of the tub. Thus all regions of a whirlpool tub critical for contamination are subjected to the influence of the heated mist-like medium.

As one feature of the method according to the invention, the mist-like medium is produced by vaporizing a liquid under the influence of temperature. For this purpose, water, preferably demineralized water, is primarily employed. As a further feature of the method according to the invention, a vaporization process that takes place under normal atmospheric pressure is preferred. This has the advantage that an electrically heated steam generator operating without pressure can be employed to produce the mist-like medium, since low steam power is required to solve the task at hand. The advantage is here that such steam generators do not include pressure vessels and consequently are not considered to be steam kettles in the technical sense. The flow through the pipe system is here effected by the volume displacement produced by the steam generator. A particular advantage of the use of hot steam is that the water is sterilized by the vaporization process so that no new germs are introduced into the pipe system from the outside even if the generated steam is introduced into the pipe system at a temperature of less than 100° C. Another advantage of this manner of proceeding in the treatment of whirlpool systems is that, instead of 30 to 40 liters of water, as was required in the past to flush the pipe systems, possibly with the addition of disinfectants, only a water quantity of between 1 and 3 liters, depending on the size of the system, is required.

As another feature of the method according to the invention it is provided that the mist-like medium is produced in that a liquid in ultra-fine dispersion is introduced into a carrier gas to form an aerosol. This manner of proceeding provides the opportunity that the volume stream required to create a flow through the pipe system is made available by the carrier gas, with the flow velocity possibly being produced by way of an appropriate pressure generator, for example, a blower. The fluid is introduced into the carrier gas stream in accurately measured quantities and in ultra-fine dispersion. The temperature level required for disinfection for the mist-like medium that has been formed by spraying liquid into the carrier gas can be attained, as a feature of the invention, in that the carrier gas is heated before the aerosol is formed. However, depending on the quantity of liquid sprayed into the carrier gas stream per unit time, the temperature of the carrier gas stream must be made higher because the spraying in of the liquid results in a reduction of the temperature in the manner of vaporization cooling. However, it is possible to set the temperature level precisely so that the resulting mist-like medium can be introduced into the pipe system at a precisely predetermined temperature.

Another feature of the invention provides that the resulting aerosol is heated before being introduced into the pipe system. Depending on the configuration of the temperature control and the quantity control for the liquid to be sprayed in, this method step can also be combined with the preceding method step, that is, the heating of the carrier gas stream before the aerosol is formed. It is, however, particularly advisable for the liquid to be sprayed onto a preferably temperature controllable vaporizer surface. This has the advantage that, on the one hand, the carrier gas stream is heated and the vaporization energy is not generated by the carrier gas stream but by the vaporizer surface. The prior spraying or atomization of the liquid accelerates the vaporization and permits better regulation.

However, if water is employed to generate the mist-like medium by forming an aerosol, care must be taken that the water itself is free of germs since in this manner of proceeding temperatures generally lie below the boiling temperature of water so that the disinfection of the employed liquid itself during the aerosol forming process is not assured with the same reliability as this is the case if the mist-like medium is generated from steam.

As another feature of the method according to the invention, it is provided that the liquid for generating the mist-like medium is a temperature resistant disinfectant, at least as an addition to water. This feature of the method has the advantage that in addition to the thermal action a chemical action also takes place. This is particularly advisable if the maximally permissible temperature is limited by the material of the surfaces to be disinfected, for example, a temperature of 80° C. must not be exceeded, although it can be expected that germs are present which are not reliably killed at this temperature level. However, it is a prerequisite that the disinfectant does not chemically decompose when heated to such temperatures. Another prerequisite is that the disinfectant employed, when in its vapor form, also when mixed with steam, is not a health risk if inhaled.

The invention further relates to a whirlpool system for implementing the method according to the invention. The system includes a basin whose walls and/or bottom are equipped with nozzles for the introduction of water and/or air and which are connected by way of pipelines with at least one pressure generator in order to charge the nozzles with water and/or air. Such a whirlpool system, which is usually constructed in the form of a tub, employs a circulating pump which sucks water from the interior of the tub through a suction line and then presses the water into the filled interior of the tub through a pressure conduit with which are connected a plurality of nozzles that are directed toward the interior of the tub. The water jet may additionally suck in air through the nozzle so that a jet composed of a mixture of water and air enters into the interior of the tub. Instead of such swirl nozzles, or also in addition to such swirl nozzles, nozzles that are connected with a blower by way of a pressure conduit may be arranged, preferably in the bottom region, so that air is introduced from the bottom through a plurality of nozzles into the filled tub. This pipeline system which is itself charged only with air comes in contact with the contents of the tub when the pressure generator is switched off and/or when, at the end of the bath, the tub is drained, with part of the tub water then being emptied into the drain pipe through the air conduits which are locked relative to the drain pipe by means of a valve.

According to the invention it is provided for such a whirlpool system that an intake conduit opens into a central pressure and/or suction conduit in the region of the pressure generator and is connected with a device for generating a heated, mist-like fluid medium. With the aid of such an arrangement it is possible to conduct the heated mist-like medium through the entire pipeline system including the circulating pump, with the medium being able to flow out of the nozzle openings as well as out of the suction openings of the circulating pump and out of the pure air nozzles disposed in the bottom. Thus it is ensured that all components that have had contact with the used bath water and which are not manually accessible are exposed to the disinfecting effect of the heated, mist-like medium. Care must merely be taken that the opening of the pressure conduit of the pressure generator is blocked against air for the disinfection process by way of a blocking device since the pressure generator for the air is generally followed directly by an electrical heating cartridge which must not come in contact with the mist-like medium. However, on the other hand, this cartridge is also arranged in such a manner that in this region the pressure conduit does not come in contact with the used bath water at any time.

As an expedient feature of the invention it is provided that the device for producing the mist-like medium is formed by a steam generator. The steam generator is here advisably configured in such a way that it operates without pressure, that is, it is only under atmospheric pressure, with the flow through the pipelines being effected exclusively by enlargements of volume within the steam generator and thus by displacement. However, if a steam generator is employed and water is used to produce the mist-like medium, care must be taken that all components coming in contact with the mist-like medium are made of materials which are reliably able to withstand temperature charges of 100° C.

In another feature of the invention, a device is provided for producing the mist-like medium. This device is characterized by a housing that is connected to the intake conduit and is equipped with at least one heating device for heating blower air and is in communication with a blower. At least one spray device for generating ultra-fine droplets preferably opens into the housing in the region of the heating device. The opening of the spray device into the intake conduit may also be provided, when seen in the direction of air flow, either upstream of the heating device or downstream of the heating device. If required, a second heating device may be provided to simplify control. In that case the liquid is sprayed into the heated air and then the heated mist-like medium is heated further by means of a second heating device up to its final treatment temperature.

Preferably, one feature provides that the spray jet is directed toward a vaporizer surface of the heating device. This accomplishes that the carrier gas stream, that is, the air introduced by way of a blower, can be heated and that the heating energy required for the vaporization is not taken away from the carrier gas again but is introduced directly over the vaporizer surface into the sprayed-on liquid so that there will be a very rapid vaporization in the manner of a film vaporization.

Since only a small stream of carrier gas is required to convey the fogged medium, for example, through a pipeline system, it is particularly advisable for the spray jet to be generated by way of a pressure-free mechanical atomization, for example, by way of a so-called oscillatory atomizer.

The invention will now be described in greater detail for an embodiment thereof and with reference to schematic drawing figures.

DESCRIPTION OF THE PREFERRED EMBODIMENT

Figure 1:
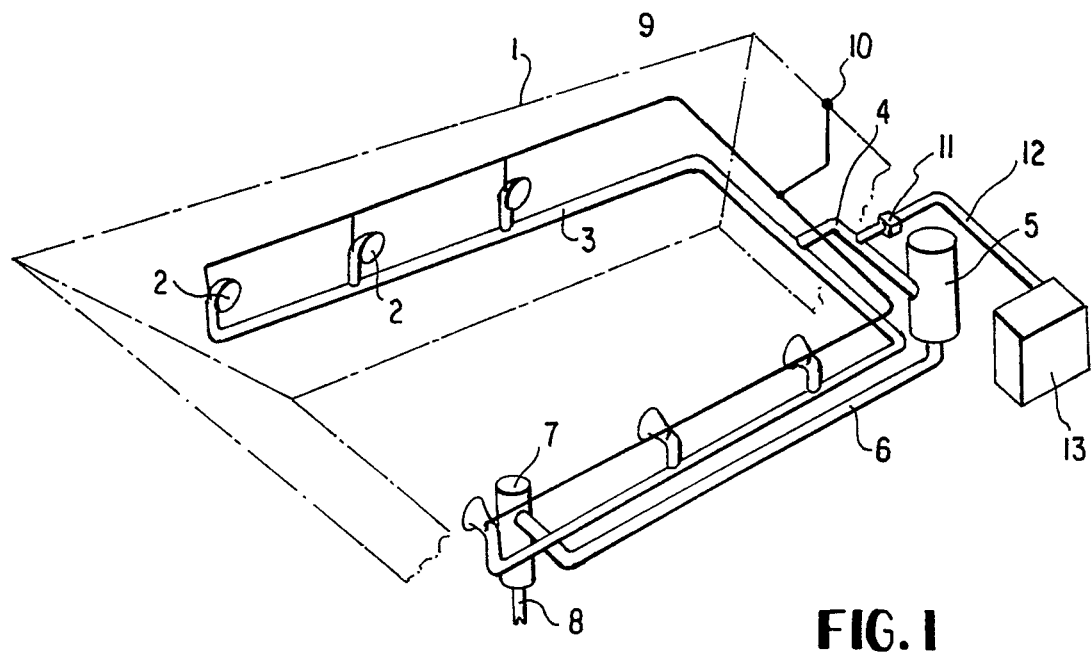
FIG. 1 depicts a whirlpool tub equipped with steam disinfection.

The whirlpool tub 1 only indicated in FIG. 1 is provided in its side walls with a plurality of swirl nozzles 2 which are in communication by way of a pressure conduit 3 with the pressure conduit 4 of a circulating pump 5. Circulating pump 5 is connected by way of a suction line 6 with a combined intake-discharge opening 7 disposed in the bottom of the tub. The combined intake-discharge opening is configured in such a way that during operation water is sucked in through suction conduit 6 from the interior of the tub and is re-introduced through swirl nozzles 2 into the filled tub interior below the surface of the water. If the drain opening is opened, the water is able to drain completely into drain pipe 8 from the interior of the tub as well as from the pipe system composed of pipe conduit 3, pressure conduit 4 and suction conduit 6.

Swirl nozzles 2 are also connected to an air duct 9 which includes an adjustable suction opening 10 disposed in the region of the tub edge so that, during operation of circulating pump 5, air is sucked in by the water jet coming out of swirl nozzles 2 and a jet composed of a water-air mixture is pressed into the interior of the tub.

Once the bath is completed, drain opening 8 is opened permitting the water to drain out completely.

By way of an intermediary check valve 11, a pipe conduit 12 is now connected with pressure conduit 4 and with a device 13 for producing a heated, mist-like medium, for example, with an electrically heatable steam generator 13. As soon as the tub and its pipe system are empty, the check valve is opened and the steam generator is put into operation. The steam generated in the steam generator is now pushed through pipe conduit 12 into pressure conduit 4 of the pipe system and then flows through pipe conduit 3 and swirl nozzles 2 into the interior of the tub. However, flow resistance causes part of the steam to flow in through the circulating pump, which is configured as a rotary pump, and through suction conduit 6 into the now open intake-discharge fixture 7 and is thus able to also flow out of the open drain opening in the tub bottom.

In this way, all regions of the pipe system including the nozzle openings and the circulating pump are touched by steam so that germs remaining in the pipeline system from the used bath water are killed already after a short time. If the tub is appropriately made of materials which are temperature resistant up to a range of, for example, above 100° C., the initial steam temperature employed may be 100° C., in which case even the swirl nozzles most remote from the point of introduction are soon subjected to a temperature of more than 90° C., thus ensuring that any existing germs will reliably be killed.

In this connection it must be considered that generally the fittings and nozzles associated with such a pipe system are made of plastics which are able to resist temperature stresses up to somewhat more than 100° C.

For this purpose, the steam generator 13 requires a connected electrical power of a maximum of 3 KW, with it being necessary to vaporize a quantity of water of no more than 3 liters for proper disinfection.

In embodiments which, in addition to or instead of swirl nozzles 2, are also equipped with bottom nozzles through which only air is introduced, an appropriate connection for the steam generator 13 to this air-carrying conduit must be provided immediately downstream of the blower so that these conduits which come in contact with the water when the blower is turned off, or also during emptying, are also exposed to the hot steam.

For both embodiments it may be advisable if an additional fresh water connection is provided so that the pipeline system can be flushed with fresh tap water immediately after the used bath water has been drained to flush out in this way initially mechanically any deposits such as skin scale, soap and dirt residues or the like. The conduits which are thus flushed with clear water practically without pressure are then charged with steam as the mist-like medium as described above.

Figure 2:
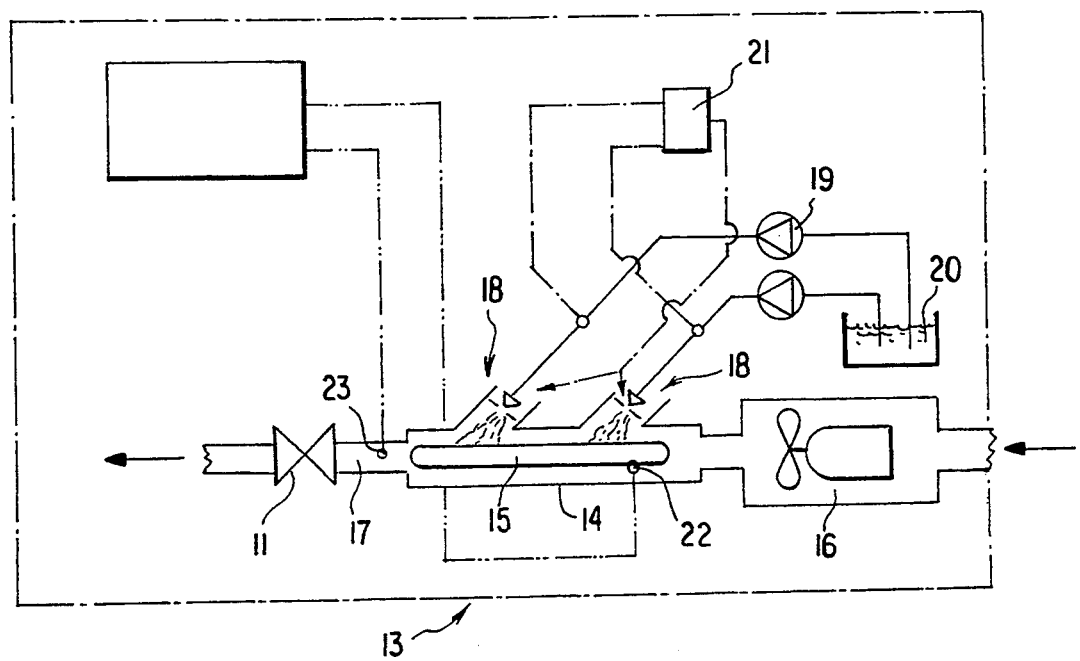
FIG. 2 depicts a device for generating a heated mist-like medium.

FIG. 2 shows a special embodiment of device 13. This device includes a vaporizer chamber 14 in which a heatable vaporizer surface 15 is disposed. The outlet of a blower 16 opens into this vaporizer chamber 14 so that air as the carrier gas is able to flow through vaporizer chamber 14. The outlet 17 of vaporizer chamber 14, which can be blocked by means of a shut-off valve 11, is connected to the system to be steam treated, for example the whirlpool tub shown in FIG. 1.

At least one spraying device 18 whose spray jet is directed toward vaporizer surface 15 opens into vaporizer chamber 14. To simplify quantity regulation, two spray devices 18 are provided here. These may be configured either as compressed air spraying devices, but preferably as pressure-free mechanical sprayers, for example as oscillating atomizers. In this embodiment, the liquid to be atomized is supplied to the system from a container disposed at a higher location or, as shown here, by means of a conveying pump 19 from a vessel 20. By way of an automatic controller 21, which is in communication with the energy supply for oscillating atomizer 18, it is ensured that the atomizer can be switched on only if the intake conduit is filled and is turned off if there is no water. The quantity regulation for an oscillating atomizer can be realized directly by an adjustment of the amplitude of the oscillating member.

The temperature of vaporizer surface 15, on the one hand, and the resulting mist-like medium, on the other hand, is detected by way of temperature sensors 22 and 23 and serves to regulate the quantity of liquid to be supplied and/or the temperature of the vaporizer surface so that the desired temperature can be maintained and/or overheating is impossible. If a higher temperature is desired in the steam treatment region, this can be accomplished by way of correspondingly heating the carrier gas, in which case, however, the sprayed-in liquid is discharged no longer as a visible mist or steam in the physical sense.

The device described in connection with FIG. 2 may also be employed to steam-treat other sanitary systems. If the heating and vaporizer output as well as the atomizer output are configured appropriately, use to steam treat a sauna cabin is also possible since here again the temperature must remain within a maximum permissible range.

I claim:

1. A method of disinfecting sanitary systems, comprising the steps of generating a heated fluid mist by vaporizing a liquid under influence of temperature at normal atmospheric pressure and applying the fluid mist to a surface to be disinfected.

2. The method as defined in claim 1, wherein the sanitary system includes a pipe system and further wherein the step of applying the fluid mist comprises the step of passing the fluid mist through the pipe system.

3. The method as defined in claim 2, wherein the sanitary system includes a whirlpool system and further wherein the step of applying the fluid mist comprises the step of exposing whirlpool system components to the fluid mist.

4. The method as defined in claim 1, wherein the step of generating the fluid mist comprises the step of introducing a liquid in ultra-fine dispersion into a carrier gas for forming an aerosol.

5. The method as defined in claim 4, further comprising the step of heating the carrier gas prior to the step of introducing.

6. The method as defined in claim 4, further comprising the step of heating the carrier gas during the step of introducing.

7. The method as defined in claim 4, further comprising the step of heating the aerosol prior to applying the aerosol to a surface to be disinfected.

8. The method as defined in claim 4, further comprising the step of regulating the quantity of the liquid prior to the introduction thereof into the carrier gas as a function of the temperature of the fluid mist.

9. The method as defined in claim 1, wherein the step of generating the fluid mist comprises the step of spraying the liquid onto a vaporizer surface and exposing the vaporizer surface to a carrier gas.

10. The method as defined in claim 9, further comprising the step of heating the carrier gas prior to the step of spraying.

11. The method as defined in claim 9, further comprising the step of heating the carrier gas during the step of spraying.

12. The method as defined in claim 1, wherein the liquid is germ-free water.

13. A whirlpool system comprising (a) a basin defined by basin walls;

(b) a pipe system including a central conduit and nozzles coupled to the central conduit and situated in the basin walls; the nozzles having outlets directed to the basin;

(c) a pressure generator coupled to said central conduit for supplying the nozzles with at least one of water and air;

(d) mist generating means for generating a fluid mist under influence of temperature at normal atmospheric pressure; and (e) an intake conduit coupling said mist generating means to said central conduit in a zone of said pressure generator for disinfecting the pipe system and the basin.

14. The whirlpool system as defined in claim 13, wherein said mist generating means comprises a vapor generator operating at normal atmospheric pressure.

15. The whirlpool system as defined in claim 13, wherein said mist generating means comprises (a) a housing coupled to said intake conduit;

(b) a blower communicating with said housing for generating an air stream passing through said housing;

(c) a heating device communicating with said housing for heating said air stream; and (d) a spraying device for generating a jet of fine liquid droplets; said spraying device opening into said housing in a zone of said heating device.

16. The whirlpool system as defined in claim 15, wherein said heating device comprises a vaporizer surface and further comprising means for directing the jet of fine liquid droplets against said vaporizer surface.

17. The whirlpool system as defined in claim 15, wherein said spraying device comprises a pressure-less mechanical atomizer.

18. The whirlpool system as defined in claim 17, wherein said atomizer is an oscillating atomizer.

19. The whirlpool system as defined in claim 15, wherein said mist generating means further comprises a regulating means for varying one of the temperature of the heating device and quantities of the liquid from which the fine liquid droplets are generated; said regulating means comprising a first temperature sensor situated at said heating device for sensing a temperature thereof and a second temperature sensor situated in said intake conduit for sensing a temperature of said fluid mist flowing therein.

* * * * *